United States Patent
Karlsson-Parra et al.

(10) Patent No.: US 9,211,321 B2
(45) Date of Patent: Dec. 15, 2015

(54) METHOD FOR PROLIFERATION OF ANTIGEN-SPECIFIC T CELLS

(75) Inventors: Alex Karlsson-Parra, Uppsala (SE); Anna-Carin Wallgren, Uppsala (SE); Bengt Andersson, Mölndal (SE)

(73) Assignee: IMMUNICUM AB, Gothenburg (SE)

( * ) Notice: Subject to any disclaimer, the term of this patent is extended or adjusted under 35 U.S.C. 154(b) by 92 days.

(21) Appl. No.: 13/504,447

(22) PCT Filed: Oct. 13, 2010

(86) PCT No.: PCT/SE2010/051099
§ 371 (c)(1),
(2), (4) Date: Jul. 10, 2012

(87) PCT Pub. No.: WO2011/053223
PCT Pub. Date: May 5, 2011

(65) Prior Publication Data
US 2012/0269860 A1    Oct. 25, 2012

Related U.S. Application Data

(60) Provisional application No. 61/255,146, filed on Oct. 27, 2009.

(30) Foreign Application Priority Data

Oct. 27, 2009   (SE) ...................................... 0950797

(51) Int. Cl.
| | |
|---|---|
| *C12N 5/00* | (2006.01) |
| *C12N 5/02* | (2006.01) |
| *A61K 38/00* | (2006.01) |
| *A61K 39/00* | (2006.01) |

(52) U.S. Cl.
CPC ..... *A61K 39/0011* (2013.01); *A61K 2039/5158* (2013.01); *A61K 2039/57* (2013.01)

(58) Field of Classification Search
None
See application file for complete search history.

(56) References Cited

U.S. PATENT DOCUMENTS

| | | | |
|---|---|---|---|
| 6,136,306 A | 10/2000 | Granger | |
| 6,274,378 B1 * | 8/2001 | Steinman et al. | 435/377 |
| 6,821,778 B1 * | 11/2004 | Engleman et al. | 435/372.3 |
| 6,977,073 B1 * | 12/2005 | Cezayirli et al. | 424/93.1 |
| 7,144,728 B1 * | 12/2006 | Suciu-Foca et al. | 435/325 |

FOREIGN PATENT DOCUMENTS

| | | |
|---|---|---|
| WO | 2008/081035 A1 | 7/2008 |
| WO | 2009/034172 A1 | 3/2009 |
| WO | 2009/053109 A1 | 4/2009 |

OTHER PUBLICATIONS

English Translation of R-1.
English Translation of R-2.
Jia Ying et al, Journal of Chongqing Medical University, 2004, vol. 29, No. 4.
Zhuang Yi-Hong, Int. J. Lab Med., Jan. 2006, vol. 27, No. 1.
Jin et al, "Allogenic lymphocyte-licensed DCs expand T cells with improved antitumor activity and resistance to oxidative stress and immunosuppressive factors", Molecular Therapy—Methods and Clinical Development, (2014) 1, 14001.

* cited by examiner

*Primary Examiner* — Michail Belyavskyi
(74) *Attorney, Agent, or Firm* — Porter, Wright, Morris & Arthur LLP; Holly Kozlowski

(57) ABSTRACT

The present invention relates to an in vitro method for priming T cells suitable for administration to a patient having a tumor. The invention is also directed to the composition obtained by the method and uses thereof.

20 Claims, 12 Drawing Sheets

A

B

METHOD FOR PROLIFERATION OF ANTIGEN-SPECIFIC T CELLS

RELATED APPLICATION

The present application is a 371 of PCT/SE2010/051099 filed Oct. 13, 2010 and claims priority under 35 U.S.C. 119 to U.S. Application No. 61/255,146 filed Oct. 27, 2009.

TECHNICAL FIELD

The present invention relates to the field of immunology and cancer therapy and more specifically to a method of activation of antigen specific T cells and the T cells produced by said method.

BACKGROUND

T cells recognize tumors or infected cells and prevent onset of disease by killing these target cells. However, the interplay of tumors or pathogens and the immune system is complex, as demonstrated by cancer or chronic infections developing in the presence of specific T cells, whereby the pathogens or tumors obviously could evade T-cell surveillance.

The ability of T cells to detect virtually any pathogenic invader is granted by its extraordinarily diverse receptor repertoire, which allows the T-cell pool to recognize a vast number of peptides upon presentation by major histocompatibility complex (MHC) molecules. Still, signaling through the T-cell receptor (TCR) (signal 1) is not sufficient for adequate T-cell activation, as costimulatory molecules provide indispensable signals for proliferation, survival, and differentiation (signal 2). In fact, naive T cells that only receive signal 1 without signal 2 are rendered anergic (unresponsive) or die through apoptosis. The integration of signals 1 and 2 is required for full T-cell activation, and the strength of these signals shapes the size of the ensuing T-cell pool. Moreover, full differentiation into effector T cells is generally dependent on a third signal, which is supplied by the antigen-presenting cell (APC) in soluble form and provides instructive signals for the type of effector T cell that is required. This 'three-signal' concept depicts a model for the activation of naive T cells and the subsequent formation of effector T cells. Yet, the immune system provides a plethora of diverse costimulatory molecules and these various types of signal 2 and 3 all contribute in their own unique manner to the quality of the T-cell response. Costimulatory signals and soluble forms of signal 3 can act on particular aspects of T-cell activation, such as survival, cell cycle progression, type of effector cell to be developed, and differentiation to either effector or memory cell.

It is now generally accepted that mature antigen-presenting dendritic cells (DCs) have to be "helped" by other lymphocytes, including CD4+ T cells NK cells and NKT cells, in order to induce long-lived memory CD8+ T cells. This "help" induces the mature DCs to differentiate further, a process known as licensing. "Helper" signals has multiple effects on DCs, including the upregulation of costimulatory molecules, the secretion of cytokines, and the upregulation of several antiapoptotic molecules, all of which cumulatively potentiate the ability of DCs to optimally activate cognate T cells, especially $CD8^+$ T cells. Moreover, "helper" lymphocytes may also express or secrete factors that directly affect T cell survival, cell cycle progression, type of effector cell to be developed, and differentiation to either effector or memory cell.

One strategy for fighting chronic infections or aggressive cancer is adoptive T-cell therapy, which involves the transfer of effector T cells to restore specific T-cell responses in the host. Recent technical developments to obtain T cells of wanted specificities have created increasing interest in using adoptive T-cell therapy in different clinical settings. Adoptive cell transfer therapy is the administration of ex vivo activated and expanded autologous tumor-reactive T cells. There are several potential advantages with the use of adoptive cell transfer therapy in cancer treatment. Tumor specific T cells can be activated and expanded to large numbers ex vivo, independently of the immunogenic properties of the tumor, and functional and phenotypic qualities of T cells can be selected prior to their adoptive transfer.

After adoptive transfer, several events must occur for T cells to cause the regression of established tumors. More specifically:—T cells must be activated in vivo through antigen specific restimulation,—the T cells must then expand to levels capable of causing the destruction of significant tumor burdens,—antitumor cells must survive long enough to complete the eradication of all tumor cells.

Previously, the criterion used to selecting cells for adoptive transfer to patients with solid tumors was the ability of the antitumor T cells to release IFN-γ and kill tumor cells upon coculture. However, it is now clear that these criteria alone do not predict in vivo efficacy. Gattinoni et al., J. Clin. Invest. 115:1616-1626 (2005), found that CD $8^+$ T cells that acquire complete effector properties and exhibit increased antitumor reactivity in vitro are less effective at triggering tumor regressions and cures in vivo.

Methods according to prior art requires restimulation one or more times to reach clinically relevant levels of tumor specific cytotoxic T cells. See for example Ho et al. (Journal of Immunological Methods, 310(2006), 40-50) and Gritzapis et al. (J. Immunol., 2008; 181; 146-154) wherein restimulation 1-2 times were necessary to reach a level of tumor specific CD8+ T cells of about 19%. Restimulation makes the cells less active and closer to apoptosis.

Consequently, there is a need for a method of preparing a T cell population for use in adoptive immunotherapy that increases proliferation and survival of antigen-specific T cells during their activation.

SUMMARY

The present invention relates to an in vitro method for priming of antigen specific T helper 1 (Th1) cells or cytotoxic T cells (CTLs) suitable for administration to a patient having a tumor. The method comprises co-culturing target T cells from the patient to be treated, autologous monocyte-derived dendritc cells, autologous or allogeneic tumor material or tumor associated proteins or peptides and allogeneic lymphocytes. The allogeneic lymphocytes are sensitized against MHC class I and/or MHC class II antigens on antigen presenting cells (APCs) from the patient or against APCs from an unrelated blood donor expressing at least one MHC class II antigen that is identical with MHC class II antigens expressed on APCs from the patient to be treated.

The present invention also relates to the antigen specific TH1 cells and/or CTLs obtainable by the method and uses thereof.

DEFINITIONS

Figure 1:
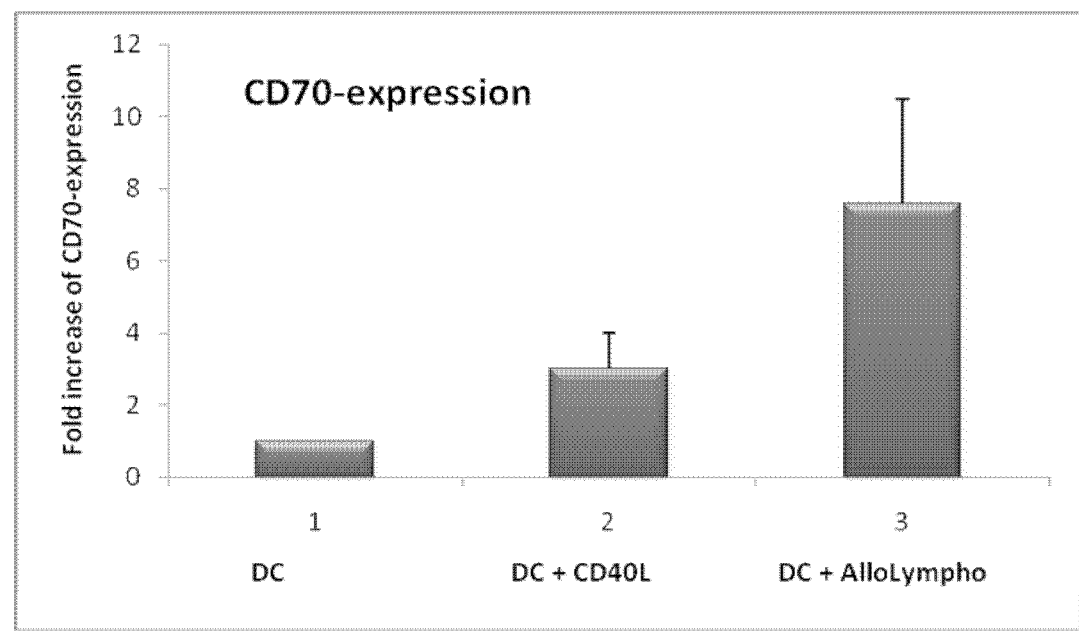
FIG. 1 illustrates that lymphocytes that have been sensitized against MHC antigens expressed on irradiated allogeneic peripheral blood mononuclear cells (PBMCs) in a conventional MLR (=allo-sensitized allogeneic lymphocytes; ASALs) markedly enhance the expression of CD70 on cocultured mature monocyte-derived DCs which are autologous with respect to the irradiated PBMCs that were used for priming of ASALs.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In the context of the present invention the term "antigen-specific" relates to the specific recognition/binding by a unique T cell receptor (TCR) of a short unique peptide sequence presented on a self MHC molecule.

In the context of the present invention the term "priming" and "activation" relates to a programmed activation process that occurs in a naïve antigen-specific T cell that become stimulated by antigen-presenting cells with or without concurrent presence of "helper" cells.

In the context of the present invention the term "responder cells" relates to different lymphocyte subpopulations, including, but not limited to, T cells, NK cells and NKT cells which respond to co-cultured allogeneic PMBCs by activation and/or proliferation.

In the context of the present invention the term "sensitized cells" relates to different lymphocyte subpopulations, including T cells, NK cells and NKT cells which have been pre-activated by co-cultured allogeneic cells, including PBMCs.

In the context of the present invention the term "target cells" relates to $CD4^+$ or $CD8^+$ T cells that become primed/activated by either allogeneic APCs or antigen-presenting autologous APCs. Sites of patient lymphocyte (target cell) collection can, for example, be peripheral blood, tumor, tumor-draining lymph node or bone marrow.

In the context of the present invention the term "mature" in relation to monocyte-derived DCs relates to their expression of "maturity-markers", including, but not limited to, CD40, CD86, CD83 and CCR7 that is induced by the stimulation of immature DCs with microbial products such as LPS or inflammatory mediators such as TNF-alpha and/or IL-1 beta.

Immature DCs are cells characterized by high endocytic activity and low T-cell activation potential. Immature DCs constantly sample the surrounding environment for pathogens such as viruses and bacteria. Immature DCs phagocytose pathogens and degrade their proteins into small pieces and upon maturation present those fragments at their cell surface using MHC molecules. Simultaneously, they upregulate cell-surface receptors that act as co-receptors in T-cell activation such as CD80, CD86, and CD40 greatly enhancing their ability to activate T-cells. They also upregulate CCR7, a chemotactic receptor that induces the dendritic cell to travel through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen specific costimulatory signals. Mature DCs probably arise from monocytes, white blood cells which circulate in the body and, depending on the right signal, can turn into either DCs or macrophages. The monocytes in turn are formed from stem cells in the bone marrow. Monocyte-derived DCs can be generated in vitro from peripheral blood monocytes.

In the context of the present invention the term "inactivation" of a cell is used to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation, such as gamma irradiation. Cells that have been fixed or permeabilized and are incapable of division are also examples of inactivated cells.

In the context of the present invention the term "mixed lymphocyte reaction", mixed lymphocyte culture", "MLR", and MLC are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLR is to provide allogeneic stimulation such as may initiate proliferation of the lymphocytes; but unless indicated, proliferation during the culture is not required. In the proper context, these terms may alternatively refer to a mixture of cells derived from such a culture.

As used herein, the term "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, and diminishment of any direct or indirect pathological consequences of the disease, preventing metastasis, lowering the rate of disease progression, amelioration or palliation of the disease state, and remission or improved prognosis.

The terms "antigen-presenting cell(s)", "APC" or "APCs" include both intact, whole cells as well as other molecules (all of allogeneic origin) which are capable of inducing the presentation of one or more antigens, preferably in association with class I MHC molecules, and all types of mononuclear cells which are capable of inducing an allogeneic immune response. Preferably whole viable cells are used as APCs. Examples of suitable APCs are, but not limited to, whole cells such as monocytes, macrophages, DCs, monocyte-derived DCs, macrophage-derived DCs, B cells and myeloid leukaemia cells e. g. cell lines THP-1, U937, HL-60 or CEM-CM3. Myeloid leukaemia cells are said to provide so called pre-monocytes.

The terms "cancer", "neoplasm" and "tumor" are used interchangeably and in either the singular or plural form, as appearing in the present specification and claims, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e. g. by such procedures as CAT scan, magnetic resonance imaging (MRI), X-ray, ultrasound or palpation. Non-limiting examples of tumors/cancers relevant for the present invention are breast cancer, glioma, glioblastoma, fibroblastoma, neurosarcoma, lung cancer, uterine cancer, lymphoma, prostate cancer, melanoma, testicular tumors, astrocytoma, ectopic hormone-producing tumor, ovarian cancer, bladder cancer, Wilm's tumor, pancreatic cancer, bone cancer, lung cancer, colorectal cancer, cervical cancer, vaginal cancer, synovial sarcoma, vasoactive intestinal peptide secreting tumors, glioblastoma, medulloblastoma, head and neck squamous cell cancer, oral cancer, oral leukoplakia, esophageal cancer, gastric cancer, or metastatic cancer, leukemia. Prostate cancer and breast cancer are particularly preferred.

In the context of the present invention the term "culturing" refers to the in vitro propagation of cells or organisms in media of various kinds. It is understood that the descendants of a cell grown in culture may not be completely identical (morphologically, genetically, or phenotypically) to the parent cell. A suitable culturing medium can be selected by the person skilled in the art and examples of such media are RPMI medium or Eagles Minimal Essential Medium (EMEM).

The terms "major histocompatibility complex" and "MHC" refer to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of a chain encoded in the MHC associated non-covalently with β2-microglobulin. Class I MHC molecules are expressed by nearly all nucleated cells and have been shown to function in antigen presentation to CD8+ T cells. Class I molecules include HLA-A, -B, and -C in humans. Class I molecules generally bind peptides 8-10 amino acids in length. Class II MHC molecules also include membrane heterodimeric proteins.

Class II MHCs are known to participate in antigen presentation to CD4+ T cells and, in humans, include HLA-DP, -DQ, and DR. Class II molecules generally bind peptides 12-20 amino acid residues in length. The term "MHC restriction" refers to a characteristic of T cells that permits them to recognize antigen only after it is processed and the resulting antigenic peptides are displayed in association with either a self class I or self class II MHC molecule.

The terms "vaccine", "immunogen", or immunogenic composition" are used herein to refer to a compound or composition that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The immunogens, and immunogenic compositions of this invention are active, which mean that they are capable of stimulating a specific immunological response (such as an anti-tumor antigen or anti-cancer cell response) mediated at least in part by the immune system of the host. The immunological response may comprise antibodies, immunoreactive cells (such as helper/inducer or cytotoxic cells), or any combination thereof, and is preferably directed towards an antigen that is present on a tumor towards which the treatment is directed. The response may be elicited or restimulated in a subject by administration of either single or multiple doses.

A compound or composition is "immunogenic" if it is capable of either: a) generating an immune response against an antigen (such as a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

Description

The present invention relates to the production of allo-sensitized allogeneic lymphocytes (ASALs) to promote increased proliferation and survival of antigen-specific T cells during their activation by autologous antigen-presenting cells, including dendritic cells (DCs).

The present invention is based on in vitro studies using PBMCs, and subpopulations thereof, from human healthy blood donors and breast cancer patients where a positive regulatory role for ASALs in the induction of antigen-specific human CD8+ T cell responses was demonstrated. Using an allogeneic in vitro model, tracking proliferation and survival of alloreactive CD8+ T cells in the presence of ASALs, the proliferative capacity was increased more that 5-fold and apoptotic cell death reduced from 10 to 5%.

Addition of ASALs leads to a strongly upregulated expression of the costimulatory molecule CD70 on antigen-presenting DCs and to production of IL-12 and IFN-gamma, two factors with a well-known positive impact on T cell commitment into type 1 CD4+ and CD8+ T cells. Further, addition of ASALs also led to production of IL-2, a well-known growth factor for T cells. Notably, CD70-mediated interactions have recently been shown to promote survival of activated T cells throughout successive rounds of division and thereby contributes to the accumulation of effector T cells.

The present invention relates to an in vitro method for priming of antigen specific T helper 1 (Th1) cells or cytotoxic T cells (CTLs) suitable for administration to a patient having a tumor. The method comprises co-culturing target T cells from the patient to be treated with autologous monocytes-derived DCs, autologous or allogeneic tumor material or tumor associated proteins or peptides and allogeneic lymphocytes sensitized against MHC class I and/or MHC class II antigens on antigen presenting cells (APCs) from the patient or against APCs from an unrelated blood donor expressing at least one MHC class II antigen that is identical with MHC class II antigens expressed on APCs from the patient to be treated.

The ASALs are responder cells obtained from a mixed leukocyte reaction and are cultured together with monocyte-derived DCs and target cells. The ASALs are allogeneic to the patient and selected from the group consisting of peripheral blood lymphocytes, including CD4+ T cells, CD8+ T cells and natural killer (NK) cells. The target cells are CD4+ and/or CD8+ T cells that are autologous to the monocyte-derived DCs. The monocyte-derived DCs are loaded with tumor material or tumor associated proteins or peptides or virus derived antigens.

Addition of ASALs further leads to an enrichment of a population of target CD8+ T cells expressing high levels of CD27. CD27+ CD8+ T cells represent potentially more effective CTLs (cytotoxic T cells) for adoptive immunotherapy since they can provide an antigen-driven autocrine signal for proliferation. Such helper-independent CD8 T cells would not require exogenous help in the form of IL-2 or CD4+ T cells to survive and expand. Thus, the present invention provides methods for treating an immune-mediated disease by providing a subject with a CD8+ T cell population that is programmed for strong cytotoxic activity in the absence or reduced presence of additional cytokines, such as IL-2, or CD4+ T cells. The methods are particularly useful for ex vivo expansion of cytolytic, antigen-specific CD8+ T cells, but may also be used for expansion of tumor-specific CD4+ T cells.

The percentage of cytolytic antigen-specific CD8+ T cells expressed as percentage of the total number of CD8+ T lymphocytes is preferably at least about 5%, more preferably at least about 10%, more preferably at least about 15%, more preferably at least about 20% and most preferably at least about 25%.

More specifically, the method of the present invention relates to an in vitro method for priming of antigen specific Th1 cells or CTLs suitable for administration to a patient having a tumor, said method comprising the following steps:
a) culturing inactivated antigen presenting cells from the patient together with peripheral blood mononuclear cells from a healthy donor,
b) culturing monocytes, from the patient, in a composition allowing the monocytes to mature to mature DCs. (the composition is further described below), and
c) culturing allo-sensitized lymphocytes, including but not limited to CD4+ T cells, CD8+ T cells and/or natural killer (NK) cells from step a) with mature DCs from step b).

The monocyte-derived DCs are obtained by first culturing monocytes in a composition comprising GM-CSF and IL-4 for about 2-7 days, preferably about 5 days to obtain immature DCs and subsequently add a second composition that enables the immature DCs to become mature DCs by culturing for at least about 12 to 72 hours and preferably about 24-48 hours. The second composition comprises components that allow the immature DCs to become mature monocyte-derived DCs that can be used to activate CD4+ and CD8+ T cells. In one embodiment the second composition comprises TNF alfa, IL-1 beta, interferon gamma, interferon beta and a TLR3 ligand, such as poly-I:C (Mailliard et al., Alpha-type-1 polarized DCs: a novel immunization tool with optimized CTL-inducing activity. *Cancer Res.* 2004; 64:5934-5937.). In another embodiment the second composition comprises interferon gamma, a TLR 3 and/or a TLR 4 ligand and a TLR7 and/or a TLR 8 ligand and/or a TLR9 ligand. Non-limiting examples of a TLR 3 ligand is poly-I:C, of a TLR7/8 ligand is R848, and of a TLR9 ligand is CpG.

The sensitization of allogeneic lymphocytes is induced by a traditional mixed leukocyte reaction (MLR or MLC—mixed leukocyte culture) comprising culturing inactivated allogeneic antigen presenting cells with peripheral blood mononuclear cells (PBMCs) from a healthy donor. The performance of an MLR is well known to the skilled person (Jordan W J, Ritter M A. Optimal analysis of composite cytokine responses during alloreactivity. *J Immunol Methods* 2002; 260: 1-14. In an MLR PBMCs (mainly lymphocytes) from two individuals are mixed together in tissue culture for several days. Lymphocytes from incompatible individuals will stimulate each other to proliferate significantly (measured for example by tritiated thymidine uptake) whereas those from compatible individuals will not. In a one-way MLC, the lymphocytes from one of the individuals are inactivated (usually by treatment with toxins, such as mitomycin or irradiation, such as gamma irradiation) thereby allowing only the untreated remaining population of cells to proliferate in response to foreign histocompatibility antigens.

The antigen presenting cells used in the MLR are selected from the group consisting of PBMCs and monocytes-derived DCs. The monocytes-derived DCs are from the patient or from a healthy donor having a MHC class II (HLA-DR) antigen matching the HLA-DR antigen of the patient.

The tumor material or tumor associated proteins or peptides are selected from the group consisting of killed tumor cells from the patient, allogeneic tumor cells of the same type as the tumor of the patient and isolated and purified tumor proteins or peptides. Isolated and purified tumor proteins or peptides are well known to the skilled person. In one embodiment the tumor material is tumor proteins loaded into the monocytes-derived DCs by transfection with mRNA encoding the tumor protein.

Examples of tumor-associated peptides are peptides derived from the HER-2 protein (associated with breast cancer), PSA (prostate specific antigen associated with prostate cancer), MART-1 protein (associated with malignant melanoma) and peptides derived from the "universal" tumor associated proteins survivin and p53, Further examples of tumor-associated peptides/proteins are well known to the person skilled in the art.

In the method of the present invention the cells are co-cultured for about 20 days, preferably for about 4 to 20 days, preferably 6 to 20 days, more preferably 7 to 14 days and most preferably about 9 to 14 days.

In one embodiment of the inventive method exogenous IL-2, IL-7, IL-15, anti-IL-4 and/or IL-21 are added to the cell culture in order to optimize cell proliferation and survival.

It is also possible to restimulate the primed antigen specific Th1 cells or CTLs by culturing said cells together with new monocytes-derived DCs, new sensitized allogeneic lymphocytes and optionally addition of exogenous IL-2, IL-7, IL-15, anti-IL-4 and/or IL-21 to the cell culture.

The present invention also relates to an immunogenic composition obtainable by the method described above as well as the antigen specific Th1 cells and/or CTLs obtainable by the method described above.

The antigen specific TH1 cells and/or CTLs are suitable for administration to a patient and preferably have at least one of the following features:
  ability to proliferate
  express the memory marker CD45 RO
  express low levels of the apoptosis marker Annexin-V (i.e. no more than 40%, preferably no more than 20%, of the cells should exhibit positive staining for Annexin-V by FACS determination)
  express CD27 and/or CD28 at their cell surface A further ability of the specific TH1 cells and/or CTLs obtainable by the method of the invention is the ability to kill tumor cells in vitro.

Further, the present invention relates to the use of antigen specific TH1 cells and/or CTLs obtainable by the method of the invention or as defined above for use in the treatment of a tumor or for eliciting an anti-tumor immunological response in a human as well as for the manufacture of a medicament for the treatment of a tumor or for eliciting an anti-tumor immunological response in a human. The TH1 cells and/or CTLs can be administered after the first stimulation or alternatively after restimulation. In one embodiment the TH1 cells and/or CTLs are administered in combination with a therapeutic cancer vaccine.

Methods of using T cell populations for adoptive cell therapy in treatment of human subjects are known to clinicians skilled in the art. T cell populations prepared according to the methods described herein and known in the art can be used in such methods. For example, adoptive cell therapy using tumor-infiltrating lymphocytes, with MART-I antigen specific T cells have been tested in the clinic (Powell et al., Blood 105:241-250, 2005). Patients with renal cell carcinoma have been vaccinated with irradiated autologous tumor cells. Harvested cells were secondarily activated with anti-CD3 monoclonal antibody and IL-2, then readministered to the patients (Chang et al., J. Clinical Oncology 21:884-890, 2003.)

Antigen-primed T cells undergo increased proliferation and decreased apoptosis upon re-stimulation when exposed to ASALs during their initial DC-mediated priming in vitro. Thus, methods for enhancing secondary T cell responses upon vaccination if adoptively transferred back to the patient before and/or during vaccination are also contemplated by the present invention.

The present invention also provides a method of preparing a T cell population for use in adoptive immunotherapy comprising T cells engineered (by viral transduction, transfection, electroporation or other methods of introducing genetic material) to express a T cell receptor or a chimeric T cell receptor that recognize the target antigen; activating these engineered T cells with antigen-loaded DCs in the presence of sensitized allogeneic lymphocytes; expanding these cells in culture; and reintroducing these cells back into the patient.

The present invention also provides methods for improving cancer vaccine therapy. Many tumors express foreign antigens that can potentially serve as targets for destruction by the immune system. Cancer vaccines generate a systemic tumor-specific immune response in a subject that comprises both humoral and cellular components. The response is elicited from the subject's own immune system by administering a vaccine composition at a site distant from the tumor or at the site of a localized tumor. The antibodies or immune cells bind the tumor antigen and lyse the tumor cells. However, there remains a need for increased T cell-responsiveness upon vaccination of cancer patients. Adoptive transfer of preactivated apoptosis-resistant tumor-specific T cells with high proliferative potential before, or at the time of vaccination, may therefore enhance vaccine-mediated immune responses in vivo.

The composition according to the invention can also be administered in combination with a therapeutic cancer vaccine. Non-limiting examples of such therapeutic cancer vaccines are ex vivo-propagated and tumor-loaded DCs, cytokine producing tumor cells, DNA-vaccination and vaccines using TLR-ligands in combination with tumor antigens.

The cells obtainable by the method of the invention can be administered directly to an organism, such as a human, to increase proliferation and survival of antigen-specific T cells during their activation. Administration of these cells, often with pharmaceutically acceptable carriers, is by any of the routes normally used for introducing a cell into ultimate contact with a mammal's blood or tissue cells.

Formulations suitable for parenteral administration, such as, for example, by intravenous, intramuscular, intradermal, intraperitoneal, subcutaneous and intratumoral routes and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous administration is the preferred method of administration for the TH1 cells and the CTLs of the invention.

The dose of the TH1 cells and the CTLs administered to a patient, in the context of the present invention should be sufficient to enhance the immune response in the patient. Thus, cells are administered to a patient in an amount sufficient to elicit an effective immune response to the tumor antigen and/or to alleviate, reduce, cure or at least partially arrest symptoms and/or complications from the disease. An amount adequate to accomplish this is defined as a "therapeutically effective dose". The dose will be determined by the activity of the cells produced and the condition of the patient, as well as the body weight or surface area of the patient to be treated. In determining the effective amount of the cell to be administered in the treatment or prophylaxis of diseases such as cancer the physician needs to evaluate progression of the disease and the induction of immune response against any relevant tumor antigens.

There are several major advantages of the invention compared to methods of the prior art. The present invention provides a high level of tumor specific CD8⁺ T cells without the need of restimulation. Restimulation makes the cells less active and brings them closer to apoptosis. Thus, a method that efficiently expands tumor specific T cells without the need for restimulation is an advantage. In addition, without the need to restimulate the cells, the tumor specific T cells can be brought back to the patient in a shorter period of time and it is more cost efficient. Further, with the use of the method according to the present invention there is no need for depletion of suppressor cells or the addition if exogenous growth factors which are very costly processes.

The invention is further illustrated by the following non-limiting examples.

EXAMPLES

Example 1

Material & Methods:

Allosensitized allogeneic lymphocytes (ASALs) were generated in a standard one-way mixed leukocyte reaction (MLR) by co-culturing gamma irradiated PBMC from a healthy blood donor with non-irradiated PBMCs from an allogeneic donor (with respect to the healthy blood donor) at a ratio of 1:1 in serum-free X-VIVO 15 medium in tissue culture flasks for 5-7 days. For propagation of immature DCs, peripheral blood mononuclear cells (PBMCs) obtained from healthy blood donors were isolated on density gradients (Lymphoprep, Nycomed, Oslo, Norway). Isolated PBMCs were resuspended in AIM-V medium (Invitrogen, Paisley, UK), plated in 24-well plastic culture plates at $2.5 \times 10^6$ cells per well and allowed to adhere for 2 hours. Non-adherent cells were removed and the remaining adherent monocytes, were cultured in AIM-V medium supplemented with recombinant human GM-CSF and IL-4 (R&D Systems, Abingdon, UK; both at 1,000 U/mL) for 4-6 days. Maturation of immature DC was induced by supplementing the culture media with IFN-α (3,000 U/mL), IFN-γ (1,000 U/mL), TNF-α (50 ng/mL), IL-1β (25 ng/mL) (all from R&D Systems) and p-I:C (Sigma-Aldrich; 20 μg/mL) during the last 24 hours of incubation.

The mature DC populations all contained more than 70% CD83+ DCs as determined by FACS analysis.

After washing, mature DCs were cocultured with non-irradiated or gamma-irradiated (25 Grey) ASALs in X-VIVO 15 medium for 24 h and analysed by FACS. Sensitization of alloreactive lymphocytes was performed by conducting a primary one-way MLR in serum-free culture media (X-VIVO 15) for 5-6 days with gamma-irradiated PBMCs as stimulator cells and non-irradiated PBMCs as responder cells. PE-conjugated anti-human CD70 was used for FACS studies.

Results:

As shown in FIG. 1, ASALs markedly enhance the expression of CD70 on mature monocyte-derived DCs which are autologous with respect to the irradiated PBMCs used for priming of ASALs.

Figure 2:
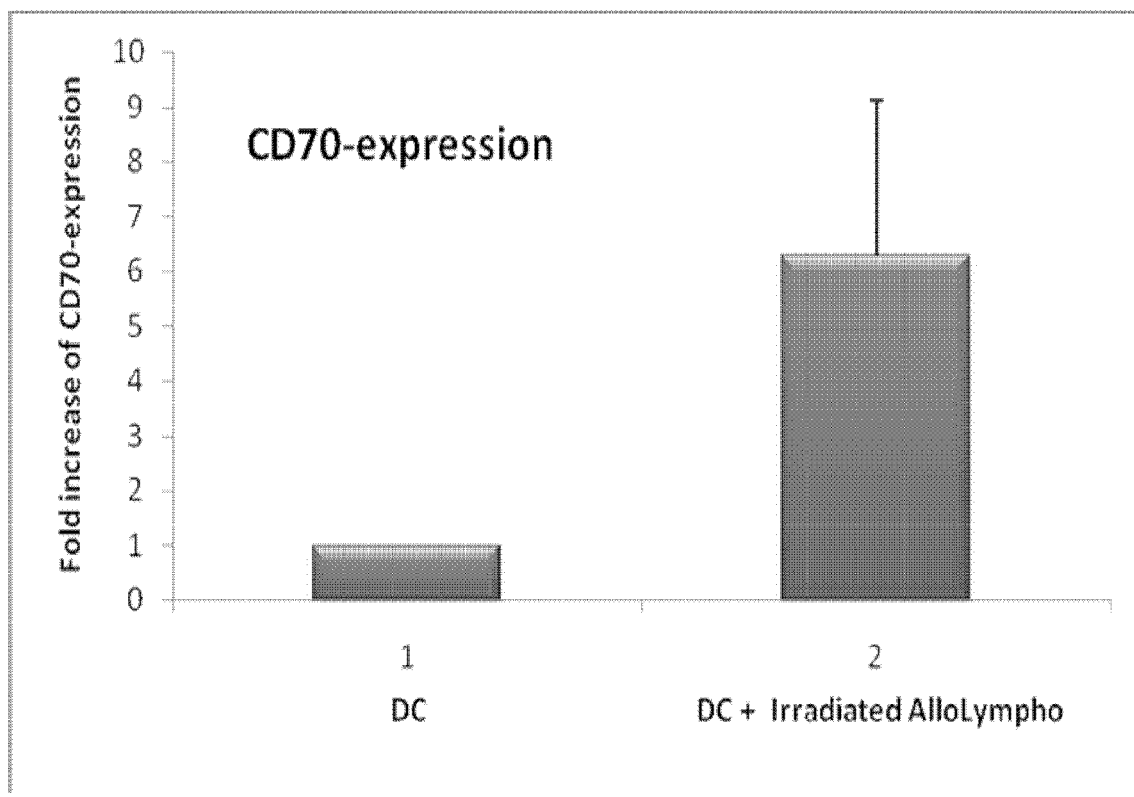
FIG. 2 illustrates that gamma-irradiated ASALs enhance the expression of CD70 on cocultured mature monocyte-derived DCs which are autologous with respect to the irradiated PBMCs used for priming of ASALs.

As shown in FIG. 2, gamma-irradiated ASALs similarly enhance the expression of CD70 on mature monocyte-derived DCs which are autologous with respect to the irradiated PBMCs used for priming of ASALs.

Figure 3:
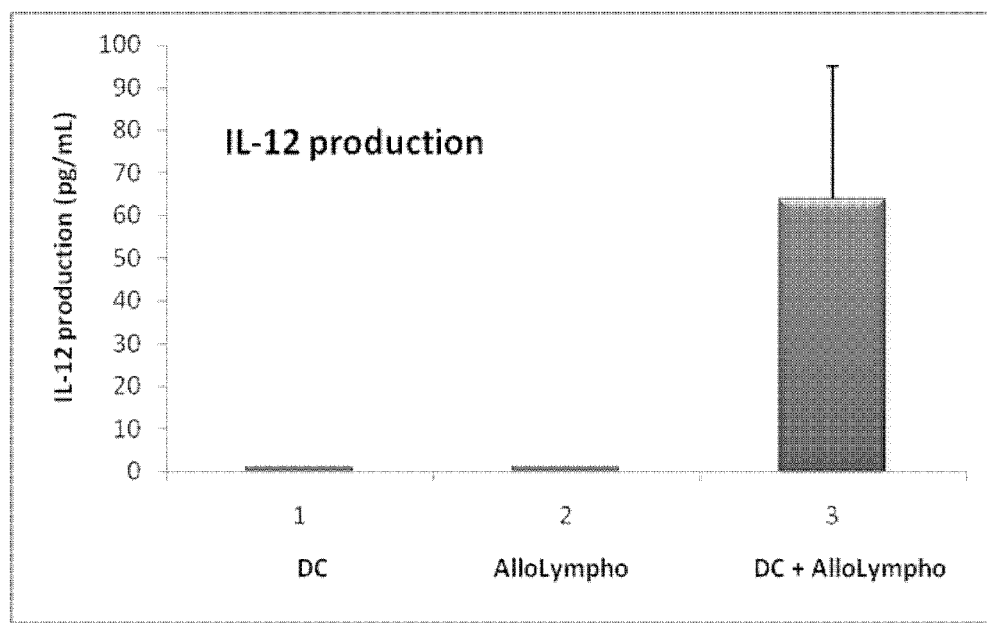
FIG. 3 illustrates that coculture of ASALs with monocyte-derived DCs which are autologous with respect to the irradiated PBMCs used for priming of ASALs induce substantial IL-12 production.
Figure 4:
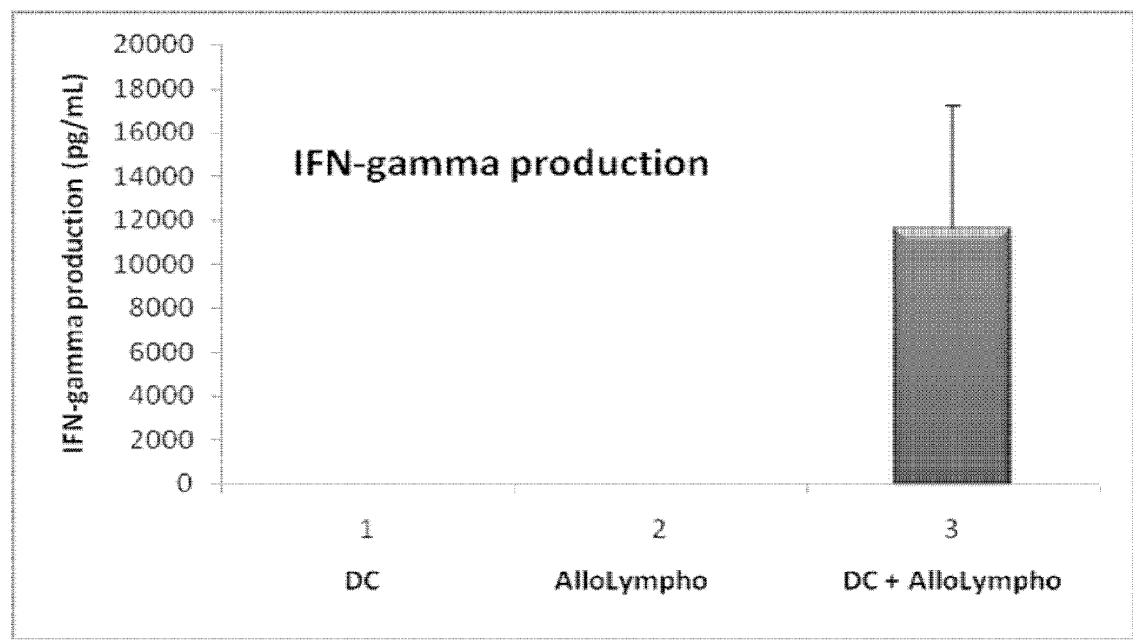
FIG. 4 illustrates that coculture of ASALs with monocyte-derived DCs which are autologous with respect to the irradiated PBMCs used for priming of ASALs induce substantial IFN-gamma production.
Figure 5:
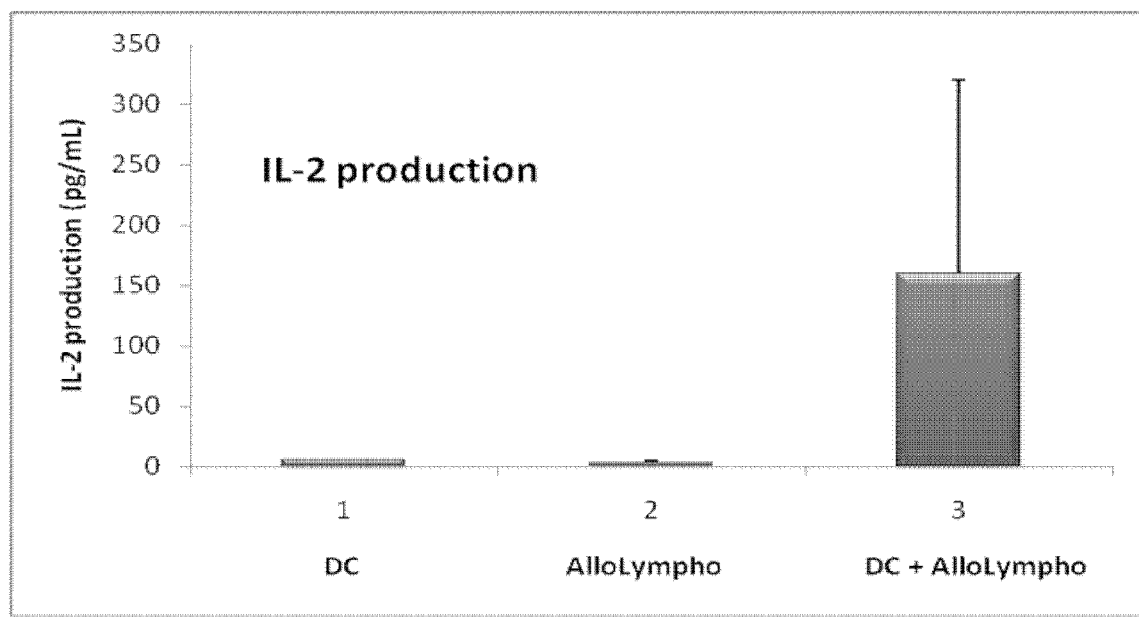
FIG. 5 illustrates that co-culture of ASALs with monocyte-derived DCs which are autologous with respect to the irradiated PBMCs used for priming of ASALs, induce substantial IL-2 production.

As shown in FIGS. 3, 4 and 5 coculture of ASALs with mature DCs which are autologous with respect to the irradiated PBMCs used for priming of ASALs, induce a substantial production of IL-12, IFN-gamma and IL-2.

Example 2

Material and Methods:

ASALs were generated during a conventional MLR for 7 days using irradiated allogeneic PBMCs as stimulators (see Example 1). After harvest and irradiation, the bulk population of ASALs ("MLR") or ASALs depleted of CD4⁺, CD8⁺ or CD56⁺ (NK/NKT) cells were cocultured with mature allogeneic monocoyte-derived DCs (autologous with respect to the PBMCs used for priming of ASALs). Coculture supernatants were collected after 24 h and subsequently assayed for IL-2, IL-12 and IFN-gamma production.

Figure 6:
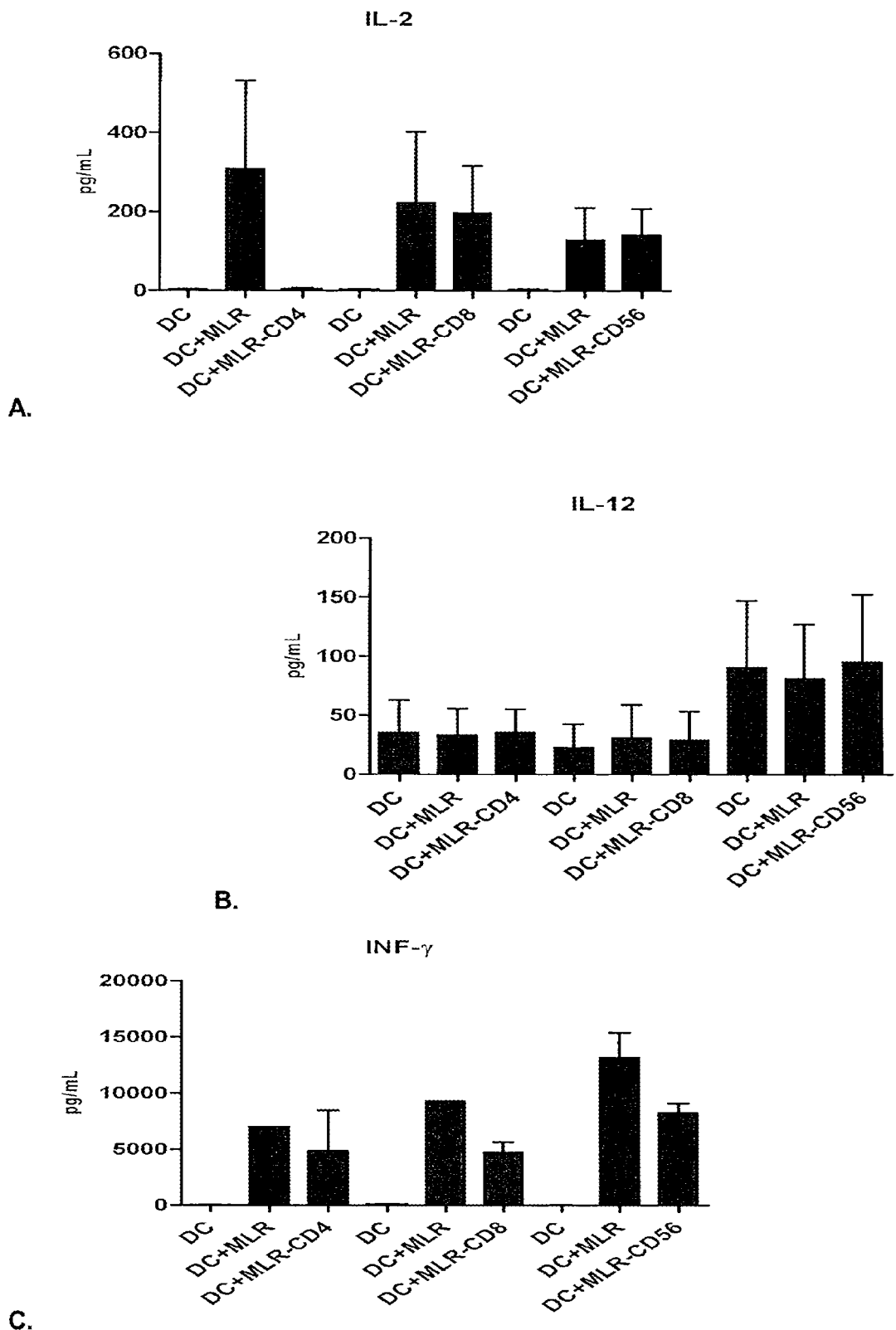
FIG. 6 illustrates the production of IL-2, IL-12 and IFN-gamma and as a result of coculture of mature monocyte-derived DCs with ASALs that have been depleted of $CD4^+$, $CD8^+$ or $CD56^+$ lymphocytes.

Results:

IL-2 production was found to be strictly CD4-dependent (FIG. 6A), while IL-12 production (FIG. 6B) showed no ASAL-dependence at all and IFN-gamma production (FIG. 6C) showed partial dependence on cocultured and alloprimed CD4⁺, CD8⁺ and CD56⁺ (NK/NKT) within the ASAL-population.

Example 3

Material and Methods:

Immature DCs were generated by plastic adherence of monocytes. Monocytes were cultured for 7 days in CellGro® DC supplemented with IL-4 and GM-CFS, both at 1000 U/mL. Maturation of DCs was induced by the addition of 50 ng/mL TNF-α, 25 ng/mL IL-1 (3, 50 ng/mL IFN-γ, 3000 U/mL IFN-α and 20 μg/mL Poly I:C during the last 2 days of incubation.

ASALs were generated in a one-way mixed lymphocyte reaction by co-culturing gamma irradiated allogenic PBMC and non-irradiated autologous PBMC, with respect to DC donor, at a ratio of 1:1 in X-VIVO 15 for 7 days.

CD8⁺ T lymphocytes were isolated by positive selection from autologous PBMC which had been cultured in X-VIVO 15 supplemented with 50 ng/mL IL-15 at a final concentration of $0.5 \times 10^6$ lymphocytes/mL for 7 days. PBMC were centrifuged and re-suspended in PBS-0.5% BSA-2M EDTA at a final concentration of $1 \times 10^7$/80 μL. PBMC were incubated with CD8⁺ MicroBeads (Miltenyi Biotec) for 15 min at 4° C., washed, re-suspended and placed onto a LS MACS column. Unlabeled cells were washed through and total effluent containing CD8⁺ lymphocytes were collected. Isolated CD8⁺ T lymphocytes were resuspended in pre-warmed PBS-1% BSA to a concentration of $1 \times 10^6$/mL and stained with 10 μM CFSE (Molecular probes Invitrogen) for 10 min at 37° C. Staining was terminated by addition of 5 mL ice-cold X-VIVO 15 medium and incubated on ice for 5 min. Cells were washed twice in medium and re-suspended to a final concentration of $1 \times 10^6$/mL. Stained CD8⁺ T lymphocytes were co-cultured for 4-7 days with irradiated allosensitized allogenic PBMC and matured autologous DC at a ratio of 4:4:1. Following culture, lymphocytes were harvested and stained with CD3-APC-H7, CD8-PerCP, CD27-APC and Annexin V. The percentage of proliferating CD8⁺ T lymphocytes was determined by flow cytometry and expressed as percentage of total lymphocytes.

Figure 7:
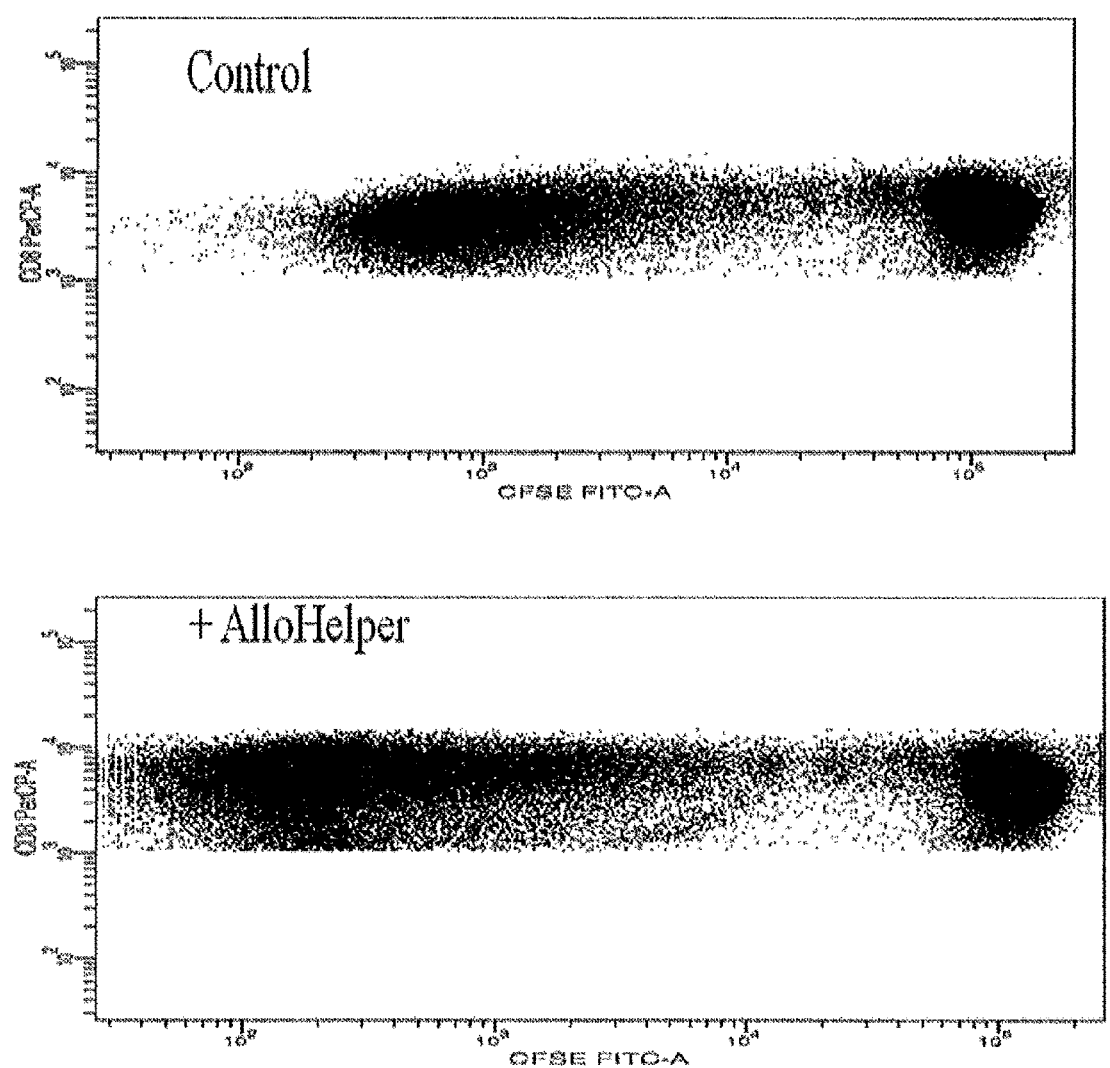
FIG. 7 illustrates that coculture of ASALs with monocyte-derived DCs, which are autologous with respect to the irradiated PBMCs that were used for priming of ASALs, increase the proliferative response in non-sesitized allogeneic $CD8^+$ T cells.

Results:

Results: As illustrated in FIG. 7, addition of irradiated "AlloHelpers" (=ASALs) strongly increase CD8+ T cell divisions (more cells with low fluorescence intensity). ASALs thus augment the ability of monocyted-derived DCs to induce a proliferative response in alloreactive CD8+ T cells.

Example 4

Material and Methods:

Immature DCs were generated by plastic adherence of monocytes. Monocytes were cultured in CellGro® DC supplemented with IL-4 and GM-CFS, both at 1000 U/mL, for 7 days. Maturation of DCs was induced by the addition of 50 ng/mL TNF-α, 25 ng/mL IL-1β, 50 ng/mL IFN-γ, 3000 U/mL IFN-α and 20 μg/mL Poly I:C during the last 2 days of incubation. Non-adherent cells, i.e. the CD8+ lymphocytes, were washed and at a final concentration of $0.5 \times 10^6$/mL cultured in X-VIVO 15 supplemented with 50 ng/mL IL-15 for 7 days. Allosensitized allogenic lymphocytes were generated in a one-way mixed lymphocyte reaction (MLR) by co-culturing gamma irradiated autologous PBMC and non-irradiated allogenic PBMC, with respect to DC donor, at a ratio of 1:1 in X-VIVO 15 for 7 days.

Mature DC were harvested and loaded with 20 μg/mL HER-2 peptide (KIFGSLAFL) in X-VIVO 15 for 1 h at 37° C. Peptide loaded mature DC were used to induce autologous HER2-specific cytotoxic T lymphocytes by co-culturing DC with irradiated MLR and non-adherent PBMC at a ratio of 1:4:4. Cells were cultured in CellGro® DC with and without 50 U/mL IL-2 and 10 ng/mL IL-7 for 9 days. Following culture, cells were harvested, washed and incubated with HER-2 specific PE-conjugated pentamer (A*0201 KIFGSLAFL) for 10 min, dark, in room temperature. Cells were washed and subsequent staining using CD3-FITC and CD8-APC were preformed. The percentage of HER-2 positive cytotoxic T lymphocytes was determined by flow cytometry and expressed as percentage of the total number of CD8+ T lymphocytes.

Figure 8:
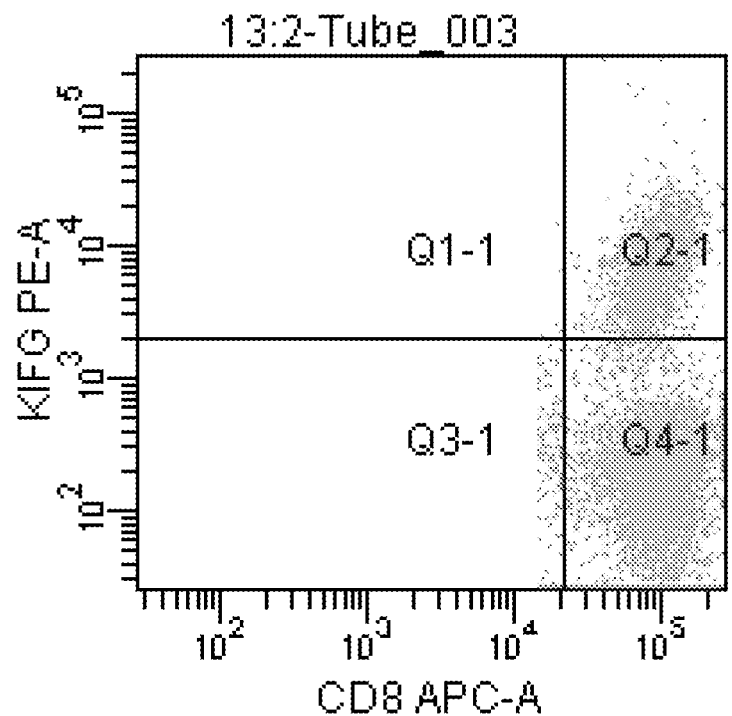
FIG. 8 shows the percentage of tumor-specific, $CD8^+$ T lymphocytes as determined by flow cytometry. A: Upper right corner shows the induction of HER-2 specific cytotoxic lymphocytes from a patient with HER-2 positive breast cancer. After 9 days of coculture with antigen-loaded autologous (with respect to $CD8^+$ target cells) DCs and irradiated ASALs, 25.2% of all $CD8^+$ target cells have become tumor specific CTLs. B: Upper right corner shows the frequency of Her2-specific cytotoxic lymphocytes in a control experiment whithout DC-loading with Her2-peptides. After 9 days of culturing only 0.4% of all $CD8^+$ T cells have become tumor specific CTLs. (Upper right corner plus lower right corner represent the total CD8 T cell population.)
Figure 8:
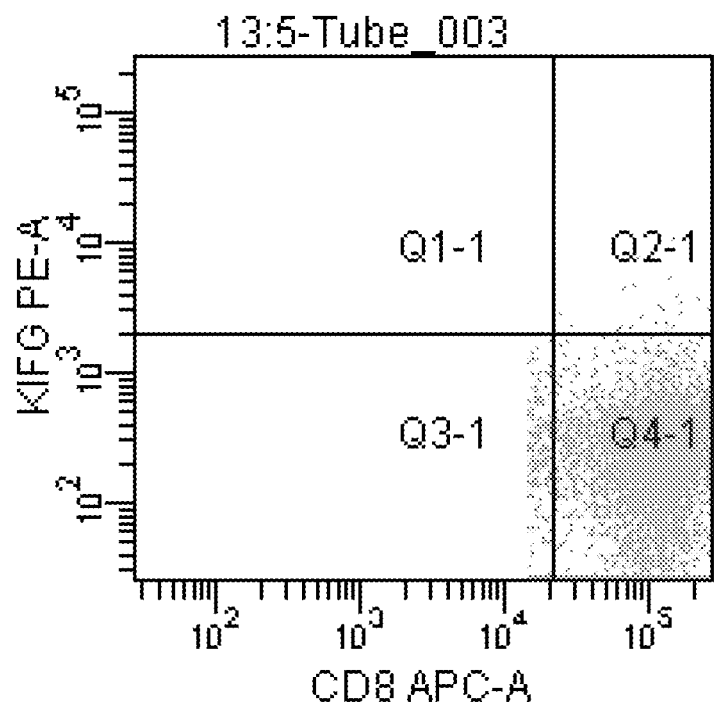

Results:

FIG. 8 shows the expansion of tumor specific CTL's that has been stimulated with autologous DC's, the allo-sensitized allogeneic lymphocytes of the invention and with Her-2 peptide (A) and without Her-2 peptideB. Her2+/CD8+ cells are shown in the upper right part of each dot plot (0.4% with alloprimed PBMCs but without DC-loading with Her2 peptides and 25.2% with alloprimed PBMCs and DC-loading with Her2 peptides (KIFG).

Compared to expansion of tumor specific CTL' in the prior art, obtaining this level of expansion after only one stimulation is extra ordinary. See for example Ho et al. (Journal of Immunological Methods, 310(2006), 40-50), wherein two restimulations were needed to obtain a 18.8% expansion of tumor specific CD8+ cells. Similarly, Gritzapis et al. (J. Immunol., 2008; 181; 146-154) needed to restimulate in order to achieve functionally expanded tumor specific CD8+ cells.

Example 5

Material and Methods: See M&M in Example 1.

CD8+ lymphocytes were isolated (using negative selection with antibody-coated magnetic beads) after coculture of DCs, irradiated ASALs (allogeneic to the DCs) for 6 days and subsequently restimulated with B-cells (autologous to the DCs used during primary stimulation) and stained for expression of CD27 and Annexin-V. Subsequent analysis was performed with FACS.

Figure 9:
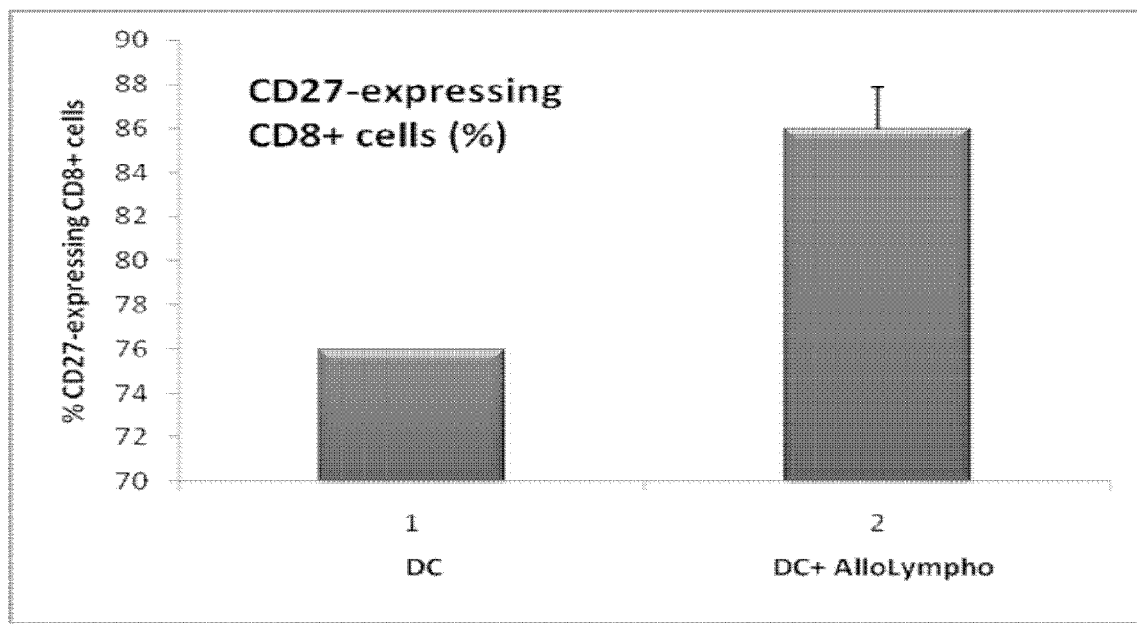
FIG. 9 illustrates that addition of irradiated ASALs to monocyte-derived DCs, which are autologous with respect to the irradiated PBMCs used for priming of ASALs, during primary stimulation of allogeneic $CD8^+$ target cells leads to increased numbers of CD27-expressing alloreactive $CD8^+$ target cells when these target cells are restimulated with B-cells that are autologous with respect to the DCs used for primary target cell stimulation.

Results:

As shown in FIG. 9, addition of ASALs during primary stimulation substantially increased expression of CD27 when the CD8+ cells were restimulated with B-cells.

Figure 10:
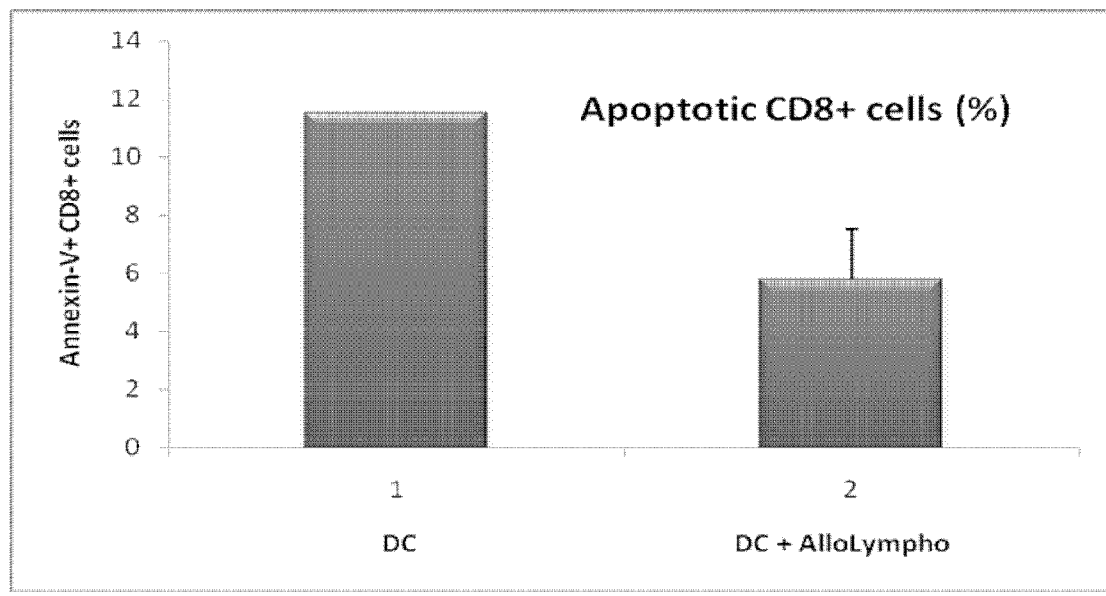
FIG. 10 illustrates that addition of irradiated ASALs to irradiated PBMCs, which are autologous with respect to the irradiated PBMCs used for priming of ASALs during primary stimulation of allogeneic $CD8^+$ target cells leads to decreased numbers of apoptotic (Annexin-V-positive) target cells when these target cells are restimulated with B-cells that are autologous with respect to the DCs used for primary target cell stimulation.

Addition of ASALs during primary stimulation substantially reduced expression of Annexin-V (apoptosis marker) when the CD8+ cells were restimulated with B-cells (see FIG. 10).

Example 6

Material and Methods: See M&M in Example 5.

Before restimulation with B-cells the primed and isolated CD8+ cells were pulsed with 3H-Thymidine.

Figure 11:
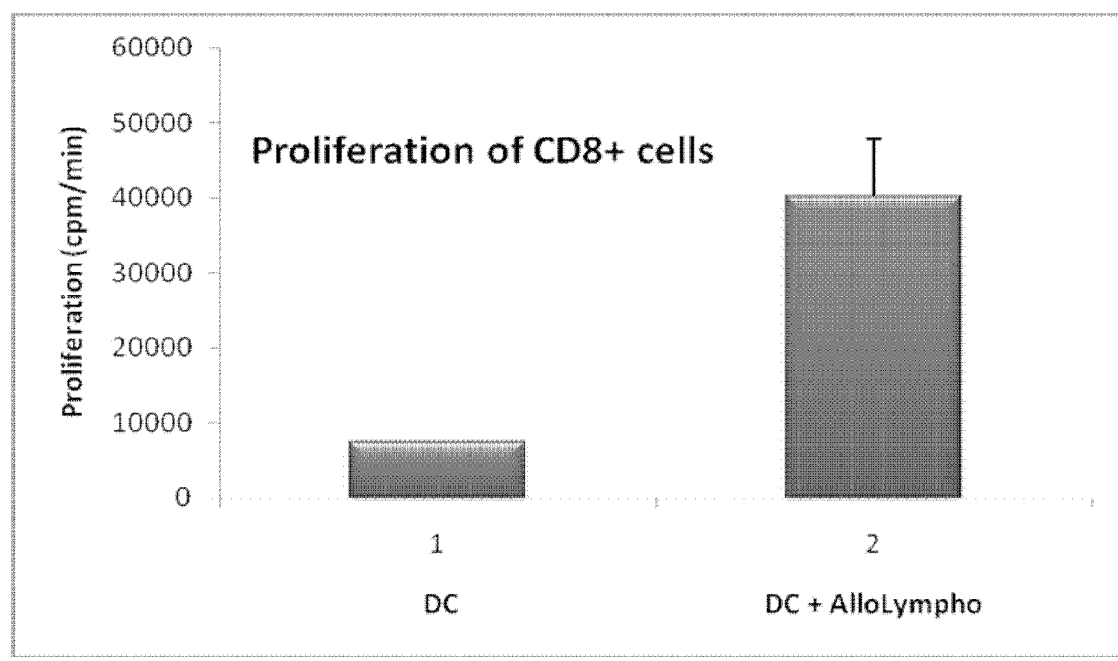
FIG. 11 illustrates that addition of irradiated ASALs to irradiated monocyte-derived DCs, which are autologous with to the irradiated PBMCs used for priming of ASALs, during primary stimulation of allogeneic $CD8^+$ target cells leads to a stronger (6-fold) secondary proliferative response when these alloreactive $CD8^+$ target cells are restimulated with B-cells that are autologous with respect to the DCs used for primary target cell stimulation.

Results:

As shown in FIG. 11, addition of ASALs during primary stimulation strongly increased the proliferative response (as measured by incorporation of 3H-Thymidine, cpm/min, day 3) of alloreactive CD8+ cells after restimulation.

Example 7

Material and Methods: See M&M in Example 5.

After coculture of B-cells and pre-activated CD8+ cells for 2 days culture supernatant was collected and analyzed for IFN-gamma production by a conventional ELISA (R&D Systems).

Figure 12:
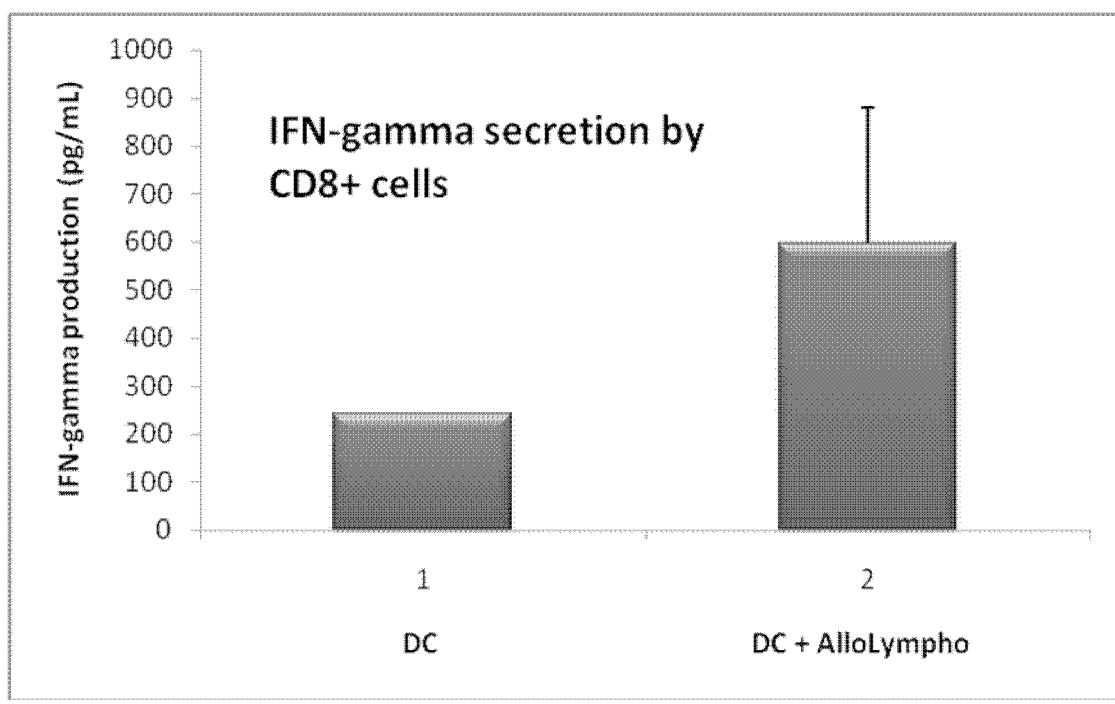
FIG. 12 illustrates that addition of irradiated ASALs to irradiated monocyte-derived DCs, which are autologous with respect to the irradiated PBMCs used for priming of ASALs, during primary stimulation of allogeneic $CD8^+$ target cells leads to a substantial increase of IFN-gamma production when these alloreactive $CD8^+$ target cells are restimulated with B-cells that are autologous with respect to the DCs used for primary target cell stimulation.

Results:

FIG. 12 shows that addition of ASALs during primary stimulation substantially increased production of IFN-gamma by alloreactive CD8+ cells after restimulation.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. An in vitro method for priming of target T cells comprising antigen specific T helper 1 (Th1) cells or cytotoxic T cells (CTLs) suitable for administration to a patient having a tumor, said method comprising co-culturing (1) target T cells from the patient to be treated, (2) monocyte-derived dendritic cells from a first healthy donor, (3) autologous or allogeneic tumor material or tumor associated proteins or peptides, and (4) allogeneic lymphocytes obtained by a mixed leukocyte reaction comprising culturing inactivated antigen presenting cells (APCs) from the first healthy donor with peripheral blood mononuclear cells (PBMCs) from a second healthy donor, wherein the APCs express at least one MHC class II antigen that is identical with an MHC class II antigen expressed on APCs from the patient to be treated, and wherein the allogeneic lymphocytes are sensitized against the APCs from the first healthy donor, wherein the sensitized allogeneic lymphocytes promote increased proliferation and/or survival of the antigen-specific Th1 cells or CTLs.

2. The method according to claim 1, wherein said antigen presenting cells in the mixed leukocyte reaction are selected from the group consisting of PBMCs and monocyte derived dendritic cells.

3. The method according to claim 2, wherein the monocyte derived dendritic cells in the mixed leukocyte reaction have a MHC class II (HLA-DR) antigen matching the HLA-DR antigen of the patient.

4. The method according to claim 1, wherein the monocyte-derived dendritic cells (2) are obtained by first culturing monocytes in a composition comprising GM-CSF and IL-4 for about 1-7 days to obtain immature dendritic cells and subsequently adding a second composition that enables the immature dendritic cells to become mature dendritic cells by culturing for at least about 12 hours.

5. The method according to claim 4, wherein the second composition comprises TNF alfa, IL-1 beta, interferon gamma, interferon alpha or beta, and a TLR3 ligand and/or a TLR 4 ligand.

6. The method according to claim 4, wherein the second composition comprises TNF alfa, interferon gamma, a TLR 3 and/or a TLR 4 ligand, and a TLR7 and/or a TLR 8 agonist.

7. The method according to claim 6, wherein the TLR 3 ligand is poly-I:C and the TLR 8 agonist is R848.

8. The method of claim 1, wherein the tumor material or tumor associated proteins or peptides are selected from the group consisting of killed tumor cells from the patient, allogeneic tumor cells of the same type as the tumor of the patient, and known isolated and purified tumor proteins or peptides.

9. The method of claim 8, wherein the tumor associated peptides are peptides derived from the HER-2 protein, PSA protein, MART-1 protein, p53 protein and/or survivin.

10. The method according to claim 8, wherein the tumor material is tumor proteins loaded into the mature dendritic cells by transfection with mRNA encoding the tumor protein.

11. The method according to claim 1, wherein the target T cells are cultured for about 4 to 20 days.

12. The method according to claim 1, wherein exogenous IL-2, IL-7, IL-15, anti-IL-4 and/or IL-21 are added to the target T cell culture.

13. The method according to claim 1, wherein the primed antigen specific Th1 cells or CTLs are restimulated by culturing said cells together with new monocyte-derived dendritic cells, new sensitized allogeneic lymphocytes and optionally addition of exogenous IL-2, IL-7, IL-15, anti-IL-4 and/or IL-21 to the cell culture.

14. The method according to claim 1, wherein the sensitized allogeneic lymphocytes comprise $CD4^+$ T cells, $CD8^+$ T cells and natural killer cells.

15. The method according to claim 5, wherein the TLR3 ligand is poly-I:C.

16. An in vitro method for priming of target T cells comprising antigen specific T helper 1 (Th1) cells or cytotoxic T cells (CTLs) suitable for administration to a patient having a tumor, said method comprising co-culturing (1) target T cells from the patient to be treated, (2) autologous monocyte-derived dendritic cells from a first healthy donor, and (3) allogeneic lymphocytes obtained by a mixed leukocyte reaction comprising culturing inactivated antigen presenting cells (APCs) from the first healthy donor with peripheral blood mononuclear cells (PBMCs) from a second healthy donor, wherein the APCs express at least one MHC class II antigen that is identical with an MHC class II antigen expressed on APCs from the patient to be treated, and wherein the allogeneic lymphocytes are sensitized against the APCs from the first healthy donor, wherein the sensitized allogeneic lymphocytes promote increased proliferation and/or survival of the antigen-specific Th1 cells or CTLs.

17. The method according to claim 16, wherein the sensitized allogeneic lymphocytes comprise $CD4^+$ T cells, $CD8^+$ T cells and natural killer cells.

18. The method according to claim 16, wherein said antigen presenting cells in the mixed leukocyte reaction are selected from the group consisting of PBMCs and monocyte derived dendritic cells.

19. The method according to claim 18, wherein the monocyte derived dendritic cells in the mixed leukocyte reaction have a MHC class II (HLA-DR) antigen matching the HLA-DR antigen of the patient.

20. The method according to claim 16, wherein the monocyte-derived dendritic cells (2) are obtained by first culturing monocytes in a composition comprising GM-CSF and IL-4 for about 1-7 days to obtain immature dendritic cells and subsequently adding a second composition that enables the immature dendritic cells to become mature dendritic cells by culturing for at least about 12 hours.

* * * * *